(12) United States Patent
Harwell

(10) Patent No.: US 6,579,831 B1
(45) Date of Patent: Jun. 17, 2003

(54) LIQUID HERBICIDAL COMPOSITIONS AND USE THEREOF IN A GRANULAR HERBICIDE

(75) Inventor: Conrad T. Harwell, Lowell, IN (US)

(73) Assignee: Nufarms Americas Inc, Burr Ridge, IL (US)

( * ) Notice: Subject to any disclaimer, the term of this patent is extended or adjusted under 35 U.S.C. 154(b) by 0 days.

(21) Appl. No.: 10/060,540

(22) Filed: Jan. 30, 2002

(51) Int. Cl.$^7$ ................ A01N 43/02; A01N 37/00; A01N 37/08; A01N 37/10
(52) U.S. Cl. ........................................ 504/127
(58) Field of Search ................ 504/116, 127, 504/128, 129, 130, 135, 140, 142, 144, 145, 146, 147

(56) References Cited

U.S. PATENT DOCUMENTS

| | | | |
|---|---|---|---|
| 3,637,366 A | | 1/1972 | Wietelmann et al. |
| 4,015,970 A | | 4/1977 | Hennart |
| 4,213,776 A | * | 7/1980 | Giilck et al. .................. 71/117 |
| 6,022,829 A | | 2/2000 | Mito |
| 6,110,866 A | | 8/2000 | Walker |

FOREIGN PATENT DOCUMENTS

| | | | |
|---|---|---|---|
| JP | 69013491 | * | 8/1965 |
| JP | 62123102 | * | 6/1987 |

* cited by examiner

*Primary Examiner*—Alton Pryor
(74) *Attorney, Agent, or Firm*—Marshall, Gerstein & Borun

(57) ABSTRACT

A concentrated, liquid herbicidal composition is disclosed. The composition contains a low volatile ester of a first herbicide, a free acid form of a second herbicide, and an aprotic solvent. A granular herbicide containing a solid substrate having the concentrated, liquid herbicidal composition applied to surfaces of the substrate also is disclosed.

21 Claims, No Drawings

LIQUID HERBICIDAL COMPOSITIONS AND USE THEREOF IN A GRANULAR HERBICIDE

FIELD OF THE INTENTION

The present invention relates to concentrated, liquid herbicidal compositions and the use thereof in a granular herbicide. More particularly, the present invention relates to a liquid herbicidal composition comprising a first herbicide having an acid functionality in the form of a low volatile ester, a second herbicide having an acid functionality in the form of a free acid, and an aprotic solvent. The herbicidal composition is applied to a solid substrate to provide a granular herbicide. The substrate comprises an inert material, like a clay, a fertilizer material, or a mixture thereof.

BACKGROUND OF THE INVENTION

Granular herbicides are important commercial products because of their ability to eliminate undesirable vegetation and their ease of application, either by hand or a mechanical means. The granular herbicide can be an herbicide applied to an inert material, like clay or ground corn cobs, or can be a combination fertilizer/herbicide, wherein the herbicide is applied to a fertilizer material, i.e., a "weed and feed" composition.

In a granular form, an herbicide is impregnated into or absorbed onto an inert material or a fertilizer material. In the granular form, the herbicide product is supplied in a plastic bag, a plastic drum, or a fiber keg. The granular herbicide product is applied to vegetation by directly spreading herbicide granules onto the vegetation at a suitable dosage rate.

It is known that certain compounds, like substituted benzoic acid herbicides and phenoxy-substituted carboxylic acid herbicides, possess selective herbicidal activity against broadleaf vegetation at dosages as low as a few ounces of active herbicide per acre. Accordingly, such herbicides are especially useful in eliminating unwanted vegetation from ornamental turf.

The substituted benzoic acid and the phenoxy-substituted carboxylic acid herbicides have been applied to susceptible vegetation in their free acid form, but herbicidal effectiveness is relatively poor because the water-insoluble free acid form of these herbicides does not sufficiently penetrate the leaves of susceptible vegetation for fast and efficient eradication. In addition, application of the free acid form of such herbicides to a solid substrate is difficult because the free acid forms are solids. Therefore, the free acid form of these herbicides either must be applied from a solution, which requires solvent removal or absorption of the solvent onto an adsorbent and/or drying agent to provide a dry granular herbicide. Alternatively, to avoid solvents, the free acid form of the herbicide must be applied as either a very finely ground powder or a melt, which requires an expensive heating step and more complex grinding, heating, and application apparatus and processes.

To improve performance, the substituted benzoic acid herbicides and the phenoxy-substituted carboxylic acid herbicides, and other herbicidal compounds having an acid functionality, traditionally are converted from the free acid form to an ester form or to a salt form. The salt and ester forms have enhanced water solubility and leaf penetration properties. Both the ester form and the salt form of these herbicidal compounds are available commercially, and are provided as liquid products containing a known, but variable, amount of the active herbicide. For concentrated products, a predetermined amount of water is added to dilute the active herbicide before spraying susceptible vegetation. The predetermined amount of water is related to the concentration of the active herbicide in the liquid herbicidal product and the desired strength of the spraying solution.

In general, the ester forms of these herbicides are provided as petroleum distillate-based emulsifiable concentrates that are diluted with water. The resulting herbicide emulsion then is sprayed on the vegetation to be controlled.

For reasons of economy and safety to the environment and the herbicide applicator, the salt forms of an herbicide often are the preferred form of these herbicides. The salt forms of these herbicides are provided as concentrated aqueous solutions that are diluted with water. However, some water-soluble, solid forms of the salt form of these herbicidal compounds also are available. The solid forms typically are water-soluble, solid products containing essentially only the herbicide (see Champion et al. U.S. Pat. No. 5,266,553), as opposed to water-insoluble granular products.

In addition, granule herbicides are prepared by impregnating a substrate with a highly concentrated aqueous solution of the herbicide salt, which often requires the addition of expensive drying agents, such a corn cob granules or silica, in order to provide a noncaking, dry granular herbicide. The highly concentrated aqueous solution of the herbicide salt used to make the granule herbicide tend to form crystals when stored at relatively cool temperatures, i.e., at temperatures below 40° F. Because the majority of granular herbicide manufacturing is done during the winter months, special heating and mixing of the aqueous herbicide concentrates prior to application onto the substrate is necessary to assure that the substrate is impregnated with the precise loading required by U.S. federal regulations.

The ester and salt forms of herbicides containing an acid functionality traditionally are applied to solid substrates, but suffer in cost and difficulty of manufacture because of the previously mentioned problems of solvent removal, and the need to utilize expensive drying agents. In addition, applying a salt form of the herbicide to a substrate often is not practical or feasible. First, applying an aqueous solution of the salt form of an herbicide to a water-soluble substrate wets substrate surfaces and makes processing difficult. Second, a solid salt form of an herbicide is difficult to apply, and especially to apply evenly, to a solid substrate. In addition, granular herbicides manufactured by adding a solid salt form of an herbicide to a substrate are hygroscopic, which causes clumping and stickiness, and requires addition of a drying agent to the composition.

Therefore, it would be advantageous to provide a highly concentrated, liquid herbicidal composition that can be applied directly to a solid substrate, without dilution or addition of drying agents, to provide a granular herbicide containing the desired herbicide combination in the desired amounts. The concentrated liquid herbicidal composition avoids the need to apply an herbicide solution or a molten herbicide to a substrate, which reduces manufacturing costs and equipment associated with preparing an herbicide solution or melting a solid herbicide, applying the molten herbicide to a solid substrate, and evaporating solvent. It also would be advantageous to provide a concentrated liquid herbicidal composition that exhibits excellent cold storage stability, and can be applied at relatively cool temperatures, compared to presentday herbicidal compositions applied to a granular substrate.

SUMMARY OF THE INVENTION

The present invention is directed to concentrated, liquid herbicidal compositions. The concentrated herbicidal compositions are used in undiluted form to prepare granular herbicides.

More particularly, the present invention is directed to a concentrated, liquid herbicidal composition comprising (a) a first herbicide having an acid functionality in the form of a low volatile ester, (b) a second herbicide having an acid functionality in the form of a free acid, and (c) an aprotic solvent. The composition comprises about 55% to about 85%, by weight, of the first herbicide, about 6% to about 35%, by weight, of the second herbicide, and about 2% to about 10%, by weight, of the aprotic solvent.

As used herein, the term "acid functionality" is defined to include a carboxylic acid functionality ($CO_2H$) and a phenolic functionality (OH).

The concentrated herbicidal composition is used in the manufacture of a granular herbicide. As used herein, the term "granular herbicide" is defined as an herbicide or mixture of herbicides absorbed, impregnated, or coated onto a solid substrate. The solid substrate can be an inert material, e.g., a clay, and/or can be a fertilizer material, e.g., urea/formaldehyde fertilizers, urea, potassium chloride, ammonium compounds, phosphorus compounds, sulfur, similar plant nutrients and micronutrients, and mixtures and combinations thereof, both synthetic and naturally occurring organic and inorganic materials.

Therefore, one aspect of the present invention is to provide a highly concentrated, liquid herbicidal composition. Another aspect of the present invention is to utilize the herbicidal composition, without dilution, in the preparation of a granular herbicide.

Yet another aspect of the present invention is to provide a liquid herbicidal composition consisting essentially of the first herbicide, the second herbicide, and the aprotic solvent, in the form of a homogeneous liquid. The herbicidal composition is free, or at least essentially free, of a protic solvent, such as an alcohol or a glycol. The absence of a protic solvent prevents the undesirable formation of esters of the second herbicide.

Another aspect of the present invention is to provide a method of preparing a granular herbicide comprising the step of applying the undiluted herbicidal composition to the surfaces of a solid substrate. The method optionally comprises a step of heating the herbicidal composition at a temperature of about 80° F. to about 100° F. to improve the flow and spray properties of the herbicidal composition, and thereby facilitate application of the herbicidal composition to the substrate, as opposed to solubilizing a solid present in the herbicidal composition.

Yet another aspect of the present invention is to provide a liquid herbicidal composition comprising a first herbicide (ester form) and a second herbicide (free acid form) independently selected from (a) a substituted benzoic acid herbicide, especially methoxy-substituted or halogen-substituted benzoic acid herbicides; (b) a phenoxy-substituted carboxylic acid herbicide, especially chlorophenoxy-substituted carboxylic acid herbicides; (c) herbicides having a nitrogen-containing heterocyclic ring and a carboxylic acid functionality, especially substituted picolinic acid and pyridine containing herbicides; and (d) miscellaneous herbicides having an acid functionality. The first and second herbicides, independently, can be, for example, triclopyr, clopyralid, 2,4-dichloro-phenoxyacetic acid (2,4-D), 2-(2,4-dichlorophenoxy)-propionic acid (2,4-DP), 2,4-dichlorophenoxybutyric acid (2,4-DB), 2-methyl-4-chlorophenoxyacetic acid (MCPA), 2-(2-methyl-4-chlorophenoxy)propionic acid (MCPP), 2-methyl-4-chlorophenoxybutyric acid (MCPB), endothall, glufosinate, glyphosate, picloram, and mixtures thereof.

The above and other aspects and advantages of the present invention will become apparent from the following detailed description of the preferred embodiments.

DETAILED DESCRIPTION OF THE PREFERRED EMBODIMENTS

A concentrated, liquid herbicidal composition of the present invention comprises (a) about 55% to about 85%, by weight, of a first herbicide having an acid functionality in the low volatile ester form, (b) about 6% to about 35%, by weight, of a second herbicide having an acid functionality in the free acid form, and (c) about 2% to about 10%, by weight, of an aprotic solvent. The concentrated herbicidal composition is used in the manufacture of a granular herbicide by applying the herbicidal composition to surfaces of a solid substrate. The solid substrate can be an inert material, or can comprise fertilizer materials.

In preferred embodiments, the first herbicide is present in an amount of about 57% to about 75%, by weight, and the second herbicide is present in an amount of about 10% to about 30%, by weight, of the composition. To achieve the full advantage of the present invention, the first and second herbicides are present in amounts of about 60% to about 70%, and about 15% to about 25%, by weight, of the composition, respectively.

In accordance with an important feature of the present invention, the first herbicide has an acid functionality that has been converted to a low volatile ester. A "low volatile ester" is known in the art as an ester form of a herbicide prepared by esterifying an acid functionality of the herbicide with an alcohol containing six to ten carbon atoms, and preferably six to eight carbon atoms. The alcohol can further contain oxygen atoms to provide ether linkages. Typical alcohols used to prepare a low volatile ester of an herbicide include, but are not limited to, decyl alcohol, octyl alcohol, 2-butoxyethanol, and 2-ethylhexyl alcohol. The first herbicide has sufficient solvency to dissolve the second herbicide, without the formation of a precipitate even when stored at cold temperatures (i.e., 10° F. and above).

In accordance with another important feature of the present invention, the second herbicide also has an acid functionality, but the acid functionality is in the free acid form, i.e., the $CO_2H$ form for a carboxylic acid or the OH form for a phenol. Both the first herbicide and second herbicide can be based on the same herbicide, e.g., 2,4-D, but in this case the first 2,4-D herbicide is in the form of a low volatile ester and the second 2,4-D herbicide is in the free acid form. Typically, the first and second herbicide are different herbicides, e.g., 2,4-D and MCPP.

In addition, the first herbicide either can be a single herbicide in the low volatile ester form or can be a mixture of herbicides in the low volatile ester form. Similarly, the second herbicide either can be a single herbicide in the free acid form or can be a mixture of herbicides in the free acid form.

As previously stated, both the first and second herbicide have an acid functionality, and can be independently selected from herbicides such as, for example, (a) substituted benzoic acid herbicides, (b) phenoxy-substituted carboxylic acid herbicides, (c) herbicides having a nitrogen-containing heterocyclic ring and a carboxylic acid functionality, and (d) miscellaneous herbicides having a carboxylic acid functionality or phenolic functionality. Specific examples of herbicides useful as first and/or second herbicides include, but are not limited to: (a) substituted benzoic acid herbicides including, but not limited to, 2-methoxy-3,6-dichlorobenzoic acid (dicamba), 2,3,6-trichlorobenzoic acid, 3,5,6-trichloro-o-anisic acid (tricamba), 3-amino-2,5-dichlorobenzoic acid (amiben), 5-2-[2-chloro-4-(trifluoromethyl)phenyoxy]-2-nitrobenzoic acid (acid form of acifluorfen), and 2,3,5-triiodobenzoic acid; (b) phenoxy-substituted carboxylic acid herbicides, including, but not limited to: 2,4-dichlorophenoxyacetic acid (2,4-D), 2,4-dichlorophenoxybutyric acid (2,4-DB), 2-(2,4-dichlorophenoxy)propionic acid (2,4-DP), 2,4,5-trichlorophenoxyacetic acid (2,4,5-T), 2-(2,4,5-trichlorophenoxy)butyric acid, 2-(2,4,5-trichlorophenoxy)propionic acid (silvex), 4-chloro-2-methylphenoxyacetic acid, (MCPA), 2-(4-chloro-2-methylphenoxy)propionic acid (MCPP), 4-(4-chloro-2-methylphenoxy)butyric acid (MCPD), and 2-[4-(2',4'-dichlorophenoxy)phenoxy] propanoic acid (diclofop); and (c) herbicides having a nitrogen-containing heterocyclic ring and a carboxylic acid functionality, and miscellaneous herbicidal compounds having a carboxylic acid functionality, including, but not limited to: 2,2-dichloropropionic acid (dalapon), 2,2,3-trichloropropionic acid, 7-oxabicyclo[2,2,1]heptane-2,3-dicarboxylic acid (endothall), (2,3,6-trichlorophenyl)acetic acid (fenac), glufosinate, gallic acid, gibberellic acid, trichloroacetic acid, β-naphthoxyacetic acid, N-(phosphonomethyl)glycine (glyphosate), 4-amino-3,5,6-trichloropicolinic acid (picloram), 3,6-dichloropicolinic acid (clopyralid), 3,5,6-trichloro-2-pyridinyloxyacetic acid (triclopyr), and 9-undecylenic acid, and broxynil.

A preferred first herbicide is a phenoxy-substituted carboxylic acid, especially an herbicide selected from the group consisting of 2,4-D, 2,4-DB, MCPP, MCPA, bromoxinyl, and mixtures thereof. The preferred ester of the first herbicide is a 2-ethylhexyl ester or a 2-butoxyethyl ester. To achieve the full advantage of the present invention, the first herbicide comprises the 2-ethylhexyl ester of 2,4-D.

A preferred second herbicide is selected from the group consisting of 2,4-D, MCPP, 2,4-DB, dicamba, picloram, clopyralid, triclopyr, bromoxynil, and mixtures thereof. To achieve the full advantage of the present invention, the second herbicide is selected from the group consisting of 2,4-D, MCPP, MCPA, dicamba, clopyralid, triclopyr, bromoxynil, and mixtures thereof.

In preferred embodiments, the concentrated herbicidal composition contains the aprotic solvent in an amount of about 2.5% to about 8%, by weight of the composition. To achieve the full advantage of the present invention, the herbicidal composition contains about 3% to about 6% of the aprotic solvent, by weight of the composition.

The amount of aprotic solvent included in a particular herbicidal composition is related to the amount and identity of the first and second herbicide in the composition. In particular, the aprotic solvent is present in a sufficient amount to provide an herbicidal composition that is a clear =solution at room temperature, i.e., 70° F., or under mild heating conditions, i.e., heating to a maximum of 100° F., and preferably to about 80° F. to about 85° F. For compositions that require slight heating to provide a clear solution, a sufficient amount of the aprotic solvent is present to provide a composition of the present invention that is a flowable viscous liquid or semisolid at room temperature and does not require heating to apply the herbicidal composition to a solid substrate. The aprotic solvent also is present in a sufficient amount to prevent the second herbicide, which typically is a solid, from precipitating from the composition.

The aprotic solvent is free of hydroxyl groups. The presence of hydroxyl groups is avoided because a solvent containing hydroxyl groups can esterify the second herbicide and change the chemical makeup of the composition. In particular, herbicides are highly regulated products, and the composition must conform to label specifications. Therefore, esterification of the second herbicide must be avoided in order to conform to label specifications. The aprotic solvent also is nonreactive, has a high solvency, has a relatively high boiling point (e.g., about 200° F. to about 250° F.) to avoid premature evaporation, and has a low odor for consumer acceptance.

Accordingly, an herbicidal composition of the present invention is free, or at least essentially free, of an alcohol. The term "essentially free of an alcohol" is defined as a composition wherein no alcohol is added intentionally. However, an alcohol can be present in the composition as a by-product or inert ingredient of a component in composition. For example, the first herbicide may contain a low percentage of unreacted alcohol from the esterification reaction required to form the first herbicide. Alternatively stated, as used herein, the term "essentially free of an alcohol" is defined as a composition containing less than 2%, typically less than 0.5%, and down to zero percent, of an alcohol.

In particular, the aprotic solvent can be, but is not limited to, N-methyl-pyrrolidone (NMP), dimethyl sulfoxide (DMSO), y-butyrolactone, dimethylformamide (DMF), hexamethylphosphoramide :(HMPA), cyclohexanone, and mixtures thereof.

A concentrated herbicidal composition of the present invention can be prepared by simply admixing the solid second herbicide with the liquid first herbicide and a sufficient amount of the aprotic solvent to provide a liquid, concentrated herbicidal composition of the present invention. The relative order of addition is not critical, e.g., the aprotic solvent can be added to the composition before or after the second herbicide is added to the first herbicide.

The effect of incorporating an aprotic solvent, e.g., NMP, into a herbicidal composition is demonstrated by the following test. In particular, three formulations containing the 2-ethylhexyl ester of 2,4-D as the first herbicide and a mixture of MCPP and dicamba as the second herbicide were prepared. NMP is present in the individual formulations in amounts of 0%, 2.91%, or 5%, by weight.

| Herbicide | Wt. %[1] | Purity %[2] | Actives[3] | Herbicide Ratio (as acid) |
|---|---|---|---|---|
| 2-Ethylhexyl ester of 2,4-D (1st herbicide) | 66.16 | 95 (as ester) 63 (as acid equivalent) | 62.85 (as ester) 41.68 (as acid equivalent) | 12.5 |
| MCPP-p acid (2nd herbicide) | 27.18 | 92 | 25.01 | 7.5 |
| DICAMBA acid (2nd herbicide) | 3.75 | 89 | 3.34 | 1 |
| NMP | 2.91 | 100 | | |
| Total | 100 | | 70.03 | |

[1]weight % in the composition on an "as is" basis, which includes the amount of any inert ingredients present in the component;
[2]the purity of each component as added to the composition, and
[3]the amount of each herbicide component in the formulation based on the ester form and/or acid form of the herbicide.

Similar compositions having a 12.5:7.5:1 weight ratio of herbicides, but containing either 0% or 5%, by weight, NMP also were prepared.

The composition containing 5% NMP was a clear solution, both immediately after manufacture and after three months storage at room temperature. The composition containing 0% NMP solidified into a stiff gel after a short storage time at room temperature. The composition containing 2.91% NMP was a clear solution after manufacture, but formed a soft, opaque, flowable semisolid after storage for three months. This semisolid was pumpable and could be applied in an undiluted form to a solid substrate to provide a granular herbicide. To facilitate application to a solid substrate, this semisolid could be heated at about 80° F. for a short time to provide a clear solution.

The following are additional examples of the present invention.

EXAMPLE 1

| Ingredient | Wt. %[1] | Purity %[2] | Actives[3] | Ratio (as acid) |
|---|---|---|---|---|
| 2,4-D, 2-ethylhexyl ester (1st herbicide) | 68.55 | 95 (as ester) 63 (as acid equivalent) | 65.12 (as ester) 43.34 (as acid equivalent) | 5 (1.666) |
| MCPP-p (2nd herbicide) | 28.22 | 92 | 26 | 3 (1.000) |
| NMP | 3.22 | 100 | | |
| Total | 100 | | 69.34 | |

The composition of Example 1 was a clear solution, and remained a clear liquid after storage at room temperature for three months.

EXAMPLE 2

| Ingredient | Wt. %[1] | Ratio (as acid) |
|---|---|---|
| 2,4-D, 2-ethylhexyl ester (first herbicide) | 86.13 | |
| 2,4-D, acid (second herbicide) | 7.21 | 25 (total 2,4-D as acid) |
| LONTREL[4] (second herbicide) | 3.01 | 1 |
| Dicamba (second herbicide) | 2.74 | 1 |
| NMP | 0.91 | |
| Total | 100 | |

[4]clopyralid (about 78% active)

EXAMPLE 3

| Ingredient | Wt. %[1] | Ratio (as acid) |
|---|---|---|
| 2,4-D, 2-ethylhexyl ester (first herbicide) | 89.19 | 20.8 |
| LONTREL[4] (second herbicide) | 3.44 | 1 |
| Dicamba (second herbicide) | 3.03 | 1 |
| NMP | 4.34 | |
| Total | 100 | |

A concentrated herbicidal composition of the present invention is used in the manufacture of granular herbicides. In particular, a present herbicidal composition is applied to a solid substrate in a sufficient amount to provide a granular herbicide of a predetermined herbicidal strength. The herbicidal concentrate is applied to the solid substrate by any method known to persons skilled in the art, and typically by spraying the herbicidal concentrate onto surfaces of the solid substrate accompanied by mixing of the solid substrate. In accordance with an important feature of the present invention, the herbicidal composition is a pumpable and sprayable composition and is applied without dilution.

The solid substrate of the granular herbicide can be an inert material, a fertilizer material, or a mixture thereof. As used herein, the term "fertilizer material" is defined as any substance capable of supplying plant nutrients, e.g., primary, secondary, and/or micronutrients, to vegetation.

The solid substrate particles typically have a major diameter of about 0.6 to about 16 mm, more preferably about 1 to about 8 mm. The total weight of the undiluted herbicidal composition applied to the solid substrate typically is about 3% to about 20% of the total weight of the granular herbicide.

Inert materials that can be used as the solid substrate include, but are not limited to, dried clay, calcium carbonate, brick, pumice, pyrophyllite, sulphur, kaolin, dolomite, plaster, wood flour, ground corn cobs, sugars, sodium chloride, sodium sulfate, sodium silicate, sodium borate, magnesia, mica, iron oxide, zinc oxide, titanium oxide, antimony oxide, cryolite, vermiculite, calcinated lime, gypsum, perlite, diatomaceous earth, bentonite clay, calcium sulfate, and mixtures thereof.

Fertilizer materials that can be used as the solid substrate include, but are not limited to, water-soluble and water-insoluble materials, like ammonium sulfate, ammonium chloride, ammonium nitrate, an ammonium phosphate, sodium nitrate, potassium nitrate, calcium nitrate, potassium chloride, potassium sulfate, potassium carbonate, a sodium phosphate, a potassium phosphate, urea, compounds capable of providing vegetation a micronutrient, such as copper, magnesium, zinc, calcium, boron, molybdenum, manganese, iron, and nickel, such as magnesium sulfate, an iron chelate, manganese sulfate, nickel sulfate, zinc sulfate, copper sulfate, animal dung fertilizers, MILORGANITE and HOUACTINITE organic fertilizers, and mixtures thereof.

The granular herbicide and the concentrated herbicidal composition also can contain various optional ingredients known to persons skilled in the art. For example, adjuvants, dedusting agents, other pesticides (e.g., insecticides or growth regulators), stabilizers, surfactants, dyes, and similar optional ingredients can be included to provide granular herbicides that are safely handled and convenient to apply accurately to areas in need of treatment. The granular herbicide is applied in an amount sufficient to assure herbicidal action. The amount applied depends on the herbicide in the herbicidal composition and the purpose for which it is being used.

A granular herbicide of the present invention is prepared as follows. When the substrate is an inert material or a single fertilizer material, the substrate is provided in a suitable size and optional ingredients can be added. If the substrate is a blend of fertilizer materials, or a fertilizer material blended with an inert material, the solid substrate first is prepared by methods known in the art, e.g., blending. In either case, the solid substrate first is provided, then the herbicidal composition then is applied to the solid substrate.

For example, a large drum-shaped vessel capable of holding a dry, solid substrate, and able to rotate at an inclined angle along the center axis, can be used. The components of the solid substrate are added to the drum during rotation to facilitate a mixing or blending action. Typically, the vessel has means for spraying a liquid herbicidal composition onto the solid substrate. Spraying serves to impregnate or coat the surfaces of the solid substrate with the liquid herbicidal composition. Often the method of incorporating the herbicidal composition onto the solid substrate involves the use of a pump and nozzles to propel small droplets of the herbicidal composition onto the solid substrate such that the herbicidal composition is evenly distributed on the solid substrate. Optionally, during the process of mixing, a small amount of an additive, such as a nonionic surfactant, can be sprayed onto the solid substrate to facilitate formation of a uniform coating on the particles of the solid substrate.

By using different amounts of a given fertilizer material, a desired level and ratio of nitrogen, phosphorus, and potassium, also known as the NPK value, can be achieved. For example, to produce a ton of a fertilizer containing an NPK value of 16-16-18 requires mixing of 700 pounds urea, 700 pounds super triple phosphate, and 600 pounds of coarse potash. This fertilizer material has an NPK composition, plus sulfur, of 22-4-12+7S, and can be used as the solid substrate of the granular herbicide.

After the fertilizer material is prepared, the undiluted, concentrated herbicidal composition is sprayed onto the dry fertilizer material. The herbicidal composition is sprayed utilizing a pump to pressurize the herbicidal composition and nozzles to control and direct the herbicidal composition spray. The herbicidal composition is applied, undiluted, in an amount of about 3% to about 20%, and typically about 3% to about 10%, by weight, of the granular herbicide. If the fertilizer material becomes damp or wet during addition of the herbicidal composition, and is difficult to manage, drying agents, such as clay, calcium sulfate, corn cob, silica powders, or vermiculite can be added in an amount of about 5 to about 50 pounds per ton of fertilizer material to facilitate manufacture of the granular herbicidal.

Many modifications and variations of the invention as hereinbefore set forth can be made without departing from the spirit and scope thereof and, therefore, only such limitations should be imposed as are indicated by the appended claims.

What is claimed is:

1. A composition comprising
   (a) about 55% to about 85%, by weight, of a first herbicide having an acid functionality in a form of a low volatile ester selected from the group consisting of a decyl ester, octyl ester, 2-ethylhexyl ester, a 2-butoxyethyl ester, and mixtures thereof;
   (b) about 6% to about 35%, by weight, of a second herbicide having an acid functionality in a form of a free acid, said second herbicide selected from the group consisting of 2-methoxy-3,6-dichlorobenzoic acid, 2,3,6-trichlorobenzoic acid, 3,5,6-trichloro-o-anisic acid, 3-amino-2,5-dichlorobenzoic acid, 5-2-[2-chloro-4-(trifluoromethyl)phenyoxy]-2-nitrobenzoic acid, 2,3,5-triiodobenzoic acid, 2,4-dichlorophenoxyacetic acid, 2,4-dichlorophenoxybutyric acid, 2-(2,4-dichlorophenoxy)propionic acid, 2,4,5-trichlorophenoxyacetic acid, 2-(2,4,5-trichlorophenoxy)butyric acid, 2-(2,4,5-trichlorophenoxy)propionic acid, 4-chloro-2-methylphenoxyacetic acid, 2-(4-chloro-2-methylphenoxy)propionic acid, 4-(4-chloro-2-methylphenoxy)butyric acid, 2-[4-(2',4'-dichlorophenoxy)phenoxy]propanoic acid, 2,2-dichloropropionic acid, 2,2,3-trichloropropionic acid, 7-oxabicyclo[2.2.1]heptane-2,3-dicarboxylic acid, (2,3,6-trichlorophenyl)acetic acid, glufosinate, gallic acid, gibberellic acid, trichloroacetic acid, β-naphthoxyacetic acid, N-(phosphonomethyl)glycine, 4-amino-3,5,6-trichloropicolinic acid, 3,6-dichloropicolinic acid, 3,5,6-trichloro-2-pyridinyloxyacetic acid, 9-undecylenic acid, bromoxytil, and mixtures thereof; and
   (c) about 2% to about 10%, by weight, of an aprotic solvent,
   wherein the composition is a clear liquid.

2. The composition of claim 1 wherein the first herbicide is present in an amount of about 57% to about 75%, by weight.

3. The composition of claim 1 wherein the first herbicide is present in an amount of about 60% to about 70%, by weight.

4. The composition of claim 1 wherein the second herbicide is present in an amount of about 10% to about 30%, by weight.

5. The composition of claim 1 wherein the second herbicide is present in an amount of about 15% to about 25%, by weight.

6. The composition of claim 1 wherein the aprotic solvent is present in an amount of about 2.5% to about 8%, by weight.

7. The composition of claim 1 wherein the aprotic solvent is present in an amount of about 3% to about 6%, by weight.

8. The composition of claim 1 wherein the composition comprises less than 2% of an alcohol.

9. The composition of claim 1 wherein the first herbicide is selected from the group consisting of a substituted benzoic acid herbicide, a phenoxy-substituted carboxylic acid herbicide, an herbicide having a nitrogen-containing heterocyclic ring and a carboxylic acid functionality, and mixtures thereof.

10. The composition of claim 1 wherein the first herbicide is a low volatile ester of a phenoxy-substituted carboxylic acid herbicide.

11. The composition of claim 1 wherein the first herbicide is selected from the group consisting of 2,4-dichlorophenoxyacetic acid, 2,4-dichlorophenoxybutyric acid, 2-(4-chloro-2-methylphenoxy)propionic acid, MCPA, 2,4-DP, bromoxynil, and mixtures thereof.

12. The composition of claim 1 wherein the second herbicide is selected from the group consisting of 2,4-dichlorophenoxyacetic acid, 2,4-dichlorophenoxybutyric acid, 2-(4-chloro-2-methylphenoxy)propionic acid, 4-amino-3,5,6-trichloropicolinic acid, 3,6-dichloropicolinic acid, 3,5,6-trichloro-2-pyridinyloxyacetic acid, 2-methoxy-3,6-dichlorobenzoic acid, bromoxynil, and mixtures thereof.

13. The composition of claim 1 wherein the aprotic solvent is selected from the group consisting of N-methylpyrrolidone, dimethyl sulfoxide, γ-butyrolactone, dimethylformamide, hexamethylphosphoramide, cyclohexanone, and mixtures thereof.

14. The composition of claim 1 wherein the first herbicide is selected from the group consisting of 2,4-dichlorophenoxyacetic acid, 2,4-dichlorophenoxybutyric acid, 2-(4-chloro-2-methylphenoxy)propionic acid, and mixtures thereof; and
   the second herbicide is selected from the group consisting of 2,4-dichlorophenoxyacetic acid, 2,4-dichlorophenoxybutyric acid, 2-(4-chloro-2-methylphenoxy)propionic acid, 4-amino-3,5,6-trichloropicolinic acid, 3,6-dichloropicolinic acid, 3,5,6-trichloro-2-pyridinyloxyacetic acid, 2-methoxy-3,6-dichlorobenzoic acid, and mixtures thereof.

15. The composition of claim 14 wherein the aprotic solvent comprises N-methyl-pyrrolidone.

16. The composition of claim 14, wherein the first herbicide is in the form of a 2-ethylhexyl ester or a 2-butoxyethyl ester.

17. The composition of claim 16 wherein the first herbicide comprises the 2-ethylhexyl ester of 2,4-dichlorophenoxyacetic acid, and the second herbicide is selected from the group consisting of 2-methoxy-3,6-dichlorobenzoic acid, 2-(4-chloro-2-methylphenoxy) propionic acid, 3,6-dichloropicolinic acid, and mixtures thereof.

18. The composition of claim 17 wherein the aprotic solvent comprises N-methyl-pyrrolidone.

19. A granular herbicide prepared by applying a composition of claim 1, in an undiluted form, to a solid substrate.

20. The granular herbicide of claim 19 wherein the solid substrate comprises an inert material, a fertilizer material, or a mixture thereof.

21. A composition consisting essentially of
   (a) about 55% to about 85%, by weight, of a first herbicide having an acid functionality in a form of a low volatile ester;
   (b) about 6% to about 35%, by weight, of a second herbicide having an acid functionality in a form of a free acid; and
   (c) about 2% to about 10%, by weight, of an aprotic solvent,
   wherein the composition is a clear liquid.

* * * * *

UNITED STATES PATENT AND TRADEMARK OFFICE
CERTIFICATE OF CORRECTION

PATENT NO. : 6,579,831 B1
DATED : June 17, 2003
INVENTOR(S) : Conrad T. Harwell

It is certified that error appears in the above-identified patent and that said Letters Patent is hereby corrected as shown below:

<u>Column 10,</u>
Line 8, "bromoxytil" should be -- bromoxynil --

Signed and Sealed this

Third Day of February, 2004

JON W. DUDAS
*Acting Director of the United States Patent and Trademark Office*